United States Patent [19]

Saito et al.

[11] Patent Number: 4,900,407

[45] Date of Patent: Feb. 13, 1990

[54] METHOD FOR DEOXYGENATION OF ALCOHOLS

[75] Inventors: Isao Saito, Kyoto; Teruo Matsuura, Kyoto; Hideyuki Ikehira, Osaka, all of Japan

[73] Assignee: Yamasa Shoyu Kabushiki Kaisha, Chiba, Japan

[21] Appl. No.: 355,814

[22] Filed: May 17, 1989

Related U.S. Application Data

[63] Continuation of Ser. No. 58,228, filed as PCT JP86/00506 on Oct. 3, 1986, published as WO87/02030 on Apr. 9, 1987, abandoned.

[30] Foreign Application Priority Data

Oct. 3, 1985 [JP]  Japan .................................. 60-220961

[51] Int. Cl.$^4$ .......................... B01J 19/08; C25B 3/04
[52] U.S. Cl. .............................. 204/73 R; 204/157.15; 204/157.6; 204/157.9
[58] Field of Search .............. 204/73 R, 75, 76, 157.6, 204/157.61, 157.87, 157.88, 157.89, 157.9, 157.15

[56] References Cited

PUBLICATIONS

Portella et al., Tetrahedron, vol. 40, No. 19, pp. 3635–3644, (1984).
Ono et al., Journal of the Electrochemical Society, vol. 101, No. 2, pp. 104–109 (1954).
Pete et al., J. Chem. Soc., Chem. Commun. 439 (1975).
Tetrahedron, vol. 39, No. 16, pp. 2639–2645 (1983).
Journal of American Chemical Society, vol. 108, No. 11, pp. 3115–3117 (1986).

Primary Examiner—John F. Niebling
Assistant Examiner—Ben C. Hsing
Attorney, Agent, or Firm—Wenderoth, Lind & Ponack

[57] ABSTRACT

In a method for deoxygenating the secondary and/or tertiary OH group(s) in an alcohol having such OH group(s), a characteristic feature thereof is that the alcohol having the OH group(s) is first converted into a substituted or unsubstituted benzoate derivative, and the benzoate derivative is then subjected to a photocatalytic reaction in the presence of an electron donor or to an electrode reaction in the presence of an electrolyte, whereby the desired compound in which the OH group(s) has (have) been selectively deoxygenated can be obtained in a high yield on an industrial scale.

9 Claims, No Drawings

METHOD FOR DEOXYGENATION OF ALCOHOLS

This application is a continuation of now abandoned application Ser. No. 058,228 filed as PCT JP86/00506 on Oct. 3, 1986, published as WO87/02030 on Apr. 9, 1987, now abandoned.

TECHNICAL FIELD

The present invention relates to a novel method for deoxygenation of alcohols.

BACKGROUND ART

In the chemical synthesis of naturally occurring substances having physiological activities or analogues thereof, a method for selective replacement of the OH group by hydrogen has become increasingly important in recent years, and various methods have been developed so far. (Reference: e.g., Tetrahedron Vol. 39, No. 16, pp. 2609~2645 (1983))

Methods for deoxygenation of alcohols of this type that have been reported to date may be roughly classified as follows.

A. A method which involves nucleophilic replacement of the OH group in the alcohol by a halogen or a mercapto group followed by reductive dehalogenation or desulfurization (hereinafter referred to as Method A);

B. A method which involves introduction into the OH group in the alcohol of a tosyl, mesyl, sulfo or O-alkylisourea group followed by reduction (hereinafter referred to as Method B); and C. A method which involves introduction into the OH group in the alcohol of (a) an O-alkylthiocarbonyl, chloroformyl, phenylselenocarbonyl or benzoyl group to add a radical, (b) a carbonyl, thiocarbamoyl, phosphono, phosphoamidoyl, sulfo or mesyl group to cause an electron-transfer reaction, or (c) a carbonyl, thiocarbonyl, trifluoromethanesulfonyl or thiocarbamoyl group, for example, to cause photoexcitation to form an intermediate radical which, in turn, undergoes $\beta$-cleavage (hereinafter referred to as Method C).

Some examples of known methods for deriving deoxyribonucleosides from ribonucleosides according to Method C are as follows.

(1) After the 3'- and 5'-position OH groups of a ribonucleoside have been protected with 1,1,3,3-tetraisopropyldisiloxane, a phenoxythiocarbonyl group is introduced into the 2'-position OH group thereof, and, through the use of 2,2'-azobisisobutyronitrile (AIBN) as an initiator, reduction is carried out with tri-n-butyltin hydride, deprotection being then carried out to obtain a 2'-deoxyribonucleoside. (Reference: J. Am. Chem. Soc., Vol. 105, pp. 4059~4065 (1983))

(2) After the 3'- and 5'-position OH groups of a ribonucleoside have been protected with a benzoyl group, a thiobenzoyl group is introduced into the 2'-position OH group thereof, and cleavage is carried out with tri-n-butyltin to obtain a 2'-deoxyribonucleoside. (Reference: J. Org. Chem., Vol. 46, pp. 4301~4304 (1981))

Among conventional methods for deoxygenation of alcohols, Methods A and B, for example, which are based in principle on ionic reactions so that reactants or intermediates are liable to be easily solvated, cannot be applied to complicated, polyfunctional compounds having sterically hindered OH groups. Further, these methods generally entail a side reaction in the substitution reaction or an elimination reaction and thus have problems of a reduction in yield of the desired compound and complicated purification procedures.

In Method C, which is based on a radical reaction, radicals are less solvated in comparison to the above stated two methods, and thus this method has an advantage in that substantially no steric hindrance occurs. Method C, however, gives rise to a pollution problem because reagents used in the reaction are toxic. Other problems with Method C are the need for using expensive reagents and that the reaction must be carried out under strictly water-free conditions.

An object of the present invention is to provide a novel method for deoxygenation of alcohols in which the problems accompanying the conventional methods have been solved, and which is therefore more suitable for industrial applications.

DISCLOSURE OF INVENTION

We have found that, by esterifying an alcohol having a secondary OH group and/or a tertiary OH group with substituted or unsubstituted benzoic acid at the secondary and/or tertiary OH group(s) to be deoxygenated and subjecting the benzoate thus obtained to a photocatalytic reaction in the presence of an electron donor or to an electrode reaction in the presence of an electrolyte, the desired compound having the OH group(s) deoxygenated (reduced) can be obtained in a notably high yield. On the basis of this finding, we have arrived at the present invention.

More specifically, the present invention provides a method for deoxygenation of an alcohol having a secondary OH group and/or a tertiary OH group by deoxygenating the secondary and/or tertiary OH group(s) which comprises subjecting the alcohol, whose secondary and/or tertiary OH group(s) to be deoxygenated have/has been esterified with substituted or unsubstituted benzoic acid, to a photocatalytic reaction in the presence of an electron donor or to an electrode reaction in the presence of an electrolyte for deoxygenation.

The method of the present invention has the advantages that (1) the desired compound can be obtained in a high yield by selectively deoxygenating the secondary and/or tertiary OH group(s); (2) the reduction can be performed without using reaction reagents and catalysts that are highly toxic, which give rise to the pollution problem, and the reagents except for a solvent can be recovered; and (3) the reaction does not require strictly water-free conditions but can be carried out in the presence of water so that no specialized facilities are required nor are particular cautions needed during operation, whereby starting materials for a water-miscible alcohol can be readily used.

Thus, the present invention provides for the first time a method for selective deoxygenation of the secondary and/or tertiary OH group(s) in an alcohol which can be suitably applied for industrial purposes.

The Best Mode for Carrying Out the Invention

The present invention will now be set forth in detail.

The reaction according to the method of the present invention can be represented by the following formula:

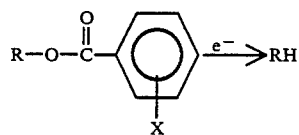

wherein R is an alcohol residue and X is hydrogen or a substituent.

The "alcohol" to be deoxygenated by the method of this invention encompasses alcohols having one or more non-phenolic secondary and/or tertiary OH groups at any position in the chemical structure thereof irrespective of the basic structure and the species of substituents. Such alcohols include a wide range of substances, for example, natural substances, chemically synthesized substances and synthetic intermediates thereof.

Specific examples of these substances are aliphatic alcohols, nucleosides, terpenes, steroids, alkaloids, macrolide antibiotics, and β-lactam antibiotics.

More specifically, examples of nucleosides are naturally occurring nucleosides such as adenosine, inosine, guanosine, xanthosine, uridine, cytidine, 2'-deoxyadenosine, 2'-deoxyguanosine, 2'-deoxyuridine, thymidine, pseudouridine, ribosylthymine, dihydrouridine, 3'-methyluridine, 4-thiouridine, 2-thiouridine, 2-thio-5-methoxycarbonyluridine, 5-methylaminomethyl-2-thiouridine, 5-methyl-2-thiouridine, uridine-5-hydroxyacetate, 2-thiocytidine, $N^4$-acetylcytidine, $N^4$-methylcytidine, 5-methylcytidine, 3-methylcytidine, $N^6$-isopentenyladenosine, $N^6$-(4-hydroxyisopentenyl)adenosine, 2-methylthio-$N^6$-isopentenyladenosine, $N^6$-carbamoylthreonineadenosine, $N^6$-methyladenosine, $N^6,N^6$-dimethyladenosine, 2-methyladenosine, 1-methyladenosine, 1-methylguanosine, 7-methylguanosine, $N^2$-methylguanosine, $N^2,N^2$-dimethylguanosine, 1-methylinosine, riboflavin, nicotinic acid riboside, kinetin riboside, S-adenosyl methionine, S-adenosyl homocysteine, $N^6$-succinyladenosine, 4-amino-5-imidazole carboxylic acid amide riboside, 1-β-D-arabinofuranosyl cytosine, 1-β-D-arabinofuranosyl thymine, 9-β-D-arabinofuranosyl adenosine, spongosine, cordycepin, angustmycins, ascamycin, aristeromycin, amicetin, aspiculamycin, 5-azacytidine, 3'-amino-3'-deoxyadenosine, 3'-acetamide-3'-deoxyadenosine, adechlorin, agelasines, oxoformycin, chryscandin, crotonoside, gougerotin, griseolic acid, coformycin, psicofuranine, sangivamycin, showdomycin, streptothricin, septacidin, tubercidin, tunicamycin, 2'-deoxycoformycin, 2'-deoxyformycin, toyocamycin, doridosine, nikkomycins, nucleocidin, uric acid-9-riboside, nebularine, neplanocin, puromycin, pyrazomycin, pillaromycin, plicacetin, blasticidin S, bredinin, polyoxins, homocitrulylaminoadenosine, formycin, mycalisine, minimycin, and lysylaminoadenosine; naturally occurring nucleosides substituted with various substituents (e.g., alkyl, alkenyl, halogenoalkyl, halogenoalkenyl, hydroxyalkyl, alkoxyalkyl, aryl, halogen, amino, alkylamino, mercapto, alkylthio, hydroxyl, alkoxyl, carbonyl, or acyl) such as 6-mercaptopurine riboside, 6-thioguanosine, 5-fluorouridine, 1-deazadenosine, 5-bromo-2'-deoxyuridine, 3'-deoxyguanosine, 9-[(2-hydroxyethoxy)methyl]guanine, 1-β-D-arabinofuranosyl-5-(E)-(2-bromovinyl)uracil, and rivabirin; or chemically or enzymatically synthesized nucleosides wherein a sugar residue or a base residue has been converted into another sugar residue or base residue.

Further examples of nucleoside derivatives are 2'-, 3'- and/or 5'-mono-, di- and/or triphosphates of the nucleosides enumerated above, for example, nucleotides such as 5'-adenylic acid, 5'-guanylic acid, 5'-inosinic acid, 5'-uridylic acid, 5'-cytidylic acid, 5'-deoxyadenylic acid, 5'-deoxyguanylic acid, 5'-deoxycytidylic acid, 5'-thymidylic acid, 3',5'-cyclic adenylic acid, 3',5'-cyclic guanylic acid, 3',5'-cyclic citydylic acid, adenosine diphosphate (ADP), guanosine diphosphate (GDP), uridine diphosphate (UDP), cytidine diphosphate (CDP), and adenosine triphosphate (ATP); and coenzymes containing the aforementioned nucleosides as their constituents, for example, nucleotide anhydrides such as nicotinamide adenine dinucleotide (NAD), flavin adenine dinucleotide (FAD), coenzyme A, active sulfuric acid (PAPS), UDP glucose, UDP glucuronic acid, UDP muramic acid, ADP glucose, GDP mannose, GDP fucose, GDP glucose, CDP choline, CDP ethanolamine, deoxy CDP choline, CDP glycerol, and CDP ribitol.

When these alcohols are subjected to the deoxygenation reaction of the present invention, the secondary and/or tertiary OH group(s) therein to be deoxygenated should be esterified with substituted or unsubstituted benzoic acid in advance in any prestep. In the case where an alcohol has two or more secondary and/or tertiary OH groups and any one of said secondary and/or tertiary OH groups is deoxygenated selectively, it is necessary to protect the remaining OH group(s), prior to the benzoic acid esterification reaction, with a suitable protective group depending upon the species of the alcohol and the position of the OH group(s) or to selectively eliminate by a suitable method, after the benzoic acid esterification reaction, a benzoate residue or residues from the OH group(s) which should not be deoxygenated. It does not matter, however, whether an alcohol has a further primary OH group and/or a phenolic OH group since the reaction proceeds selectively with respect to the secondary and tertiary OH groups in the method of the present invention.

The substituted benzoate in the phrase "substituted or unsubstituted benzoate" as contemplated herein refers to a benzoate having an electron withdrawing substituent at the meta-(m-) or para-(p-) position. Examples of such substituents are halogenoalkyl (e.g., trifluoromethyl), halogen (e.g., chlorine, bromine, iodine, and fluorine), alkyl- or arylsulfonyl (e.g., methanesulfonyl, ethanesulfonyl, and tosyl), and acyl (e.g., acetyl, propionyl, butyryl, benzoyl, and toluoyl). The use of substituted benzoates having these electron withdrawing substituents results in increased electron acceptability as compared with unsubstituted benzoates, causing the deoxygenation reaction to proceed more efficiently and providing the desired product in a higher yield.

The secondary and/or tertiary OH group(s) may be esterified with substituted or unsubstituted benzoic acid by a conventional method wherein an alcohol is reacted with the corresponding acid halide or acid anhydride of the benzoic acid as an esterifying agent. In the reaction, a solvent suitably selected according to the species of the alcohol and the esterifying agent can be used. For the reaction solvent, those commonly used in esterification reactions may be applied. Specific examples of such solvents are halogenated hydrocarbons (e.g., dichloromethane, chloroform, carbon tetrachloride, and dichloroethane), hydrocarbons (e.g., benzene, toluene, and xylene), pyridine solvents (e.g., pyridine, picoline, and lutidine), and ether solvents (e.g., ethyl ether, dioxane, and tetrahydrofuran). When a solvent other than pyridine solvents is employed, a base, such as tertiary amines (e.g., triethylamine, tripropylamine, tri-n-butylamine, and tripentylamine) and heterocyclic bases (e.g., dimethylaminopyridine and pyridine), is used as an acid neutralization reagent in combination. The esterification reaction may be ordinarily carried out at room temperature to higher temperatures for ten minutes to several hours.

The photocatalytic reaction in accordance with the method of the present invention is ordinarily carried out in a reaction solvent in the presence of an electron donor.

For the reaction solvent, hydrous or anhydrous hydrogen-donating solvents are used. Examples of such solvents are ether solvents (e.g., tetrahydrofuran, dioxane, monoglime, and diglime) and alkanol solvents (e.g., ethanol, n-propanol, iso-propanol, n-butanol, isobutanol, and pentanol). When a hydrous solvent is employed, the ratio of water to be added is suitably determined according to the species of the substance to be deoxygenated, electron donor and solvent used.

For the electron donor, any of those capable of releasing an electron upon irradiation with light rays to donate the electron to the substituted or unsubstituted benzoate group of the alcohol may be used, and a compound having an oxidation-reduction potential not exceeding about 1.3 V is applied. Examples of suitable electron donors are aromatic hydrocarbons such as anthracene, 9,10-diphenylanthracene, pyrene, 1,2,4-trimethoxybenzene, 1,2,4,5-tetramethoxybenzene, pentamethoxybenzene, 1,4-dimethoxynaphthalene, 1,8-dimethoxynaphthalene, 9-methoxyanthracene, 1,6-dimethoxypyrene, p-bis(methylthio) benzene, and p-acetoxyanisole; aromatic heterocyclic compounds such as 2,5-dimethylfuran, carbazole, N-methylcarbazole, N-ethylcarbazole, N-butylcarbazole, and N-t-butylcarbazole; olefinic compounds such as 3,4-dimethoxy-propenylbenzene, and 1-pyrrolidino-4-cyano-4-phenyl-1,3-butadiene; amines such as aniline, p-toluidine, m-toluidine, o-toluidine, p-bromoaniline, m-bromoaniline, p-chloroaniline, m-chloroaniline, o-chloroaniline, p-anisidine, m-anisidine, o-anisidine, p-aminoacetophenone, m-aminoacetophenone, o-aminoacetophenone, p-amino-N,N-dialkylaniline, p-phenylenediamine, m-phenylenediamine, o-phenylenediamine, 1-naphthylamine, 2-naphthylamine, 1-aminoanthracene, 2-aminoanthracene, 9-aminoanthracene, 2-aminophenanthrene, 9-aminophenanthrene, 1-aminopyrene, 2-aminopyrene, 6-aminopyrene, 2-aminobiphenyl, 4-aminobiphenyl, N-methylaniline, diphenylamine, N,N-dimethylaniline, N,N-dimethyl-p-chloroaniline, N,N-dimethyl-p-tolylamine, N,N-dimethyl-p-anisidine, N,N-dimethyl-m-anisidine, N,N-dimethyl-o-anisidine, N,N-diethylaniline, N,N-diethyl-p-chloroaniline, N-methyldiphenylamine, N-methyl-di-p-tolylamine, N-methyl-di-p-anisylamine, triphenylamine, 1-dimethylaminonaphthalene, 2-dimethylaminonaphthalene, and pyrrole; phenols and aminophenols such as phenol, p-cresol, m-cresol, o-cresol, p-methoxyphenol, m-methoxyphenol, o-methoxyphenol, p-hydroxyacetophenone, m-hydroxyacetophenone, o-hydroxyacetophenone, p-chlorophenol, m-chlorophenol, o-chlorophenol, hydroquinone, resorcinol, 1-naphthol, 2-naphthol, 4-phenyl-2-chlorophenol, 2,4-dichlorophenol, 2-chloro-4-bromophenol, 4-carbomethoxy-2-chlorophenol, 4-carboxy-2-chlorophenol, p-aminophenol, and p-azophenol; carboxylic acids such as anthranylic acid, m-aminobenzoic acid, and salicylic acid; and azo compounds such as hydrazobenzene, 4,4'-dichlorohydrazobenzene, and 4,4'-dimethoxyazobenzene. Any of these electron donors that is suitable for the alcohol to be deoxygenated can be used in the deoxygenation. Especially preferred is an electron donor having the property of re-accepting an electron from the radical species that has undergone β-cleavage after completion of the photocatalytic reaction. By such selection, it becomes possible to recover and reuse the electron donor. Ordinarily, the quantity of the electron donor used is 0.5 to 1.0 equivalent of the alcohol when the OH group to be deoxygenated is one.

The photocatalytic reaction can be carried out by irradiation with light rays of a wavelength in the excitation wavelength zone of the electron donor from a suitable light source such as a high-pressure or low-pressure mercury lamp or a halogen lamp. Preferably, nitrogen gas, argon gas and like inert gases are passed through the reaction system. The reaction is carried out at room temperature or higher temperatures for several hours to ten or more hours.

Further, the electrode reaction according to the method of the present invention is ordinarily conducted in a reaction solvent in the presence of an electrolyte.

For the reaction solvent, those employed in the photocatalytic reaction mentined above may be used.

The electrolyte is not limited provided that it does not impair the reaction under given voltage conditions. Examples of suitable electrolytes are tetraethylammonium chloride, tetraethylammonium bromide, tetraethylammonium iodide, tetraammonium nitrate, lithium nitrate, tetraethylammonium perchlorate, lithium perchlorate, tetraethylammonium tetrafluoroborate, lithium tetrafluoroborate, sodium acetate, lithium acetate, tetraethylammonium p-toluenesulfonate, and lithium p-toluenesulfonate.

The electrode reaction can be performed with a platinum electrode, a carbon electrode or other suitable electrodes by applying to the reaction system a current of a cathodic voltage of 1.3 V or less in the case where the voltage is constant or a certain constant current for a time period until the reaction terminates. This reaction is carried out at room temperature for several hour to ten or more hours.

The isolation and purification of the deoxygenated reaction product may be achieved by a conventional method. If deprotection is required, a deprotection reaction step suitable for the protective group may be added and, if a post-reaction step is further required, the product may be subjected to the post-reaction step.

The mechanism of the method of the present invention is outlined as follows.

An electron released from the electron donor excited by irradiation with light rays or an electron generated from the electrode is transferred to the substituted or unsubstituted benzoic acid residue of the alcohol; the electron transfer causes β-cleavage; and a radical thus formed entraps hydrogen from a hydrogen donating solvent to provide the desired deoxygenated compound.

Hereinafter, the present invention will be described in more detail with reference to specific examples of practice.

EXAMPLE 1

1 g (5.26 mmole) of m-trifluoromethylbenzoic acid was refluxed with heating for approximately 2 hours in an excess quantity of thionyl chloride. The solution was allowed to cool to room temperature and then concentrated under reduced pressure.

The residue obtained was dissolved in 10 ml of dichloromethane, and the resulting solution was added to a solution of 1.116 g (5.26 mmole) of 1,3-diphenyl-2-hydroxypropane and 0.64 g (5.26 mmole) of dimethylaminopyridine dissolved in 10 ml of dichloromethane. The mixture was caused to react for 5 hours at room temperature.

After the reaction, a saturated aqueous solution of sodium bicarbonate was added to the reaction solution, and the mixture was concentrated under reduced pressure. The residue obtained was dissolved in water-ethyl acetate, and the ethyl acetate layer was separated and concentrated under reduced pressure. The residue was adsorbed onto a silica gel column, wherepon 1.516 g of 1,3-diphenyl-2-propanol m-trifluoromethylbenzoate was isolated as an oily substance from the fraction eluted with ethyl acetate/n-hexane (15:1).

$^1$H—NMR (CDCl$_3$): δ 2.99 (d, 4H, J=6 Hz), 5.51 (t, 1H, J=6 Hz), 7.11~7.23 (m, 10H), 7.25~8.20 (m, 4H).

IR (neat): cm$^{-1}$ 1720, 1490, 1450, 1330, 1240, 1120, 1060, 750.

100 mg of 1,3-diphenyl-2-propanol m-trifluoromethylbenzoate and 52 mg of 1,2,4,5-tetramethoxybenzene were dissolved in 60 ml of a tetrahydrofuran-water mixture (10:1), and the solution was irradiated with a 100-W mercury lamp for 10 hours.

To the reaction solution was added 50 ml of a saturated aqueous solution of sodium bicarbonate, and the mixture was concentrated under reduced pressure to approximately 50 ml and extracted with ethyl acetate. The ethyl acetate layer was separated and concentrated. The residue obtained was purified through a silica gel column, whereupon 43 mg of the starting compound was recovered while 26 mg of 1,3-diphenylpropane (yield from the reacted starting compound 89%) was isolated as an oily substance.

$^1$H—NMR (CDCl$_3$): δ 1.72-2.20 (m, 2H), 2.60 (t, 4H, J=6 Hz), 6.99~7.40 (m, 10H).

IR (neat): cm$^{-1}$ 3000, 2860, 1940, 1860, 1790, 1600, 1490, 1450, 740.

EXAMPLE 2

120 mg of 1,3-diphenyl-2-propanol m-trifluorobenzoate and 57 mg of N-methylcarbazole were dissolved in 200 ml of a tetrahydrofuran-water mixture (10:1), and the solution was irradiated with a 400-W mercury lamp for 6 hours.

To the reaction solution was added 50 ml of a saturated aqueous solution of sodium bicarbonate, and the mixture was concentrated under reduced pressure to approximately 50 ml and extracted with ethyl acetate. The extract obtained was adsorbed onto a silica gel column, whereupon 56 mg of 1,3-diphenylpropane (yield 91%) was isolated as an oily substance from the fraction eluted with n-hexane/ethyl acetate (20:1).

EXAMPLE 3

1 g (6.39 mmole) of p-chlorobenzoic acid was refluxed with heating for approximately 2 hours in an excess quantity of thionyl chloride. The solution was allowed to cool to room temperature, and then concentrated under reduced pressure.

The residue obtained was dissolved in 10 ml of dichloromethane, and the resulting solution was added to a solution of 1.356 g (6.39 mmole) of 1,3-diphenyl-2-propanol and 0.78 g (6.39 mmole) of dimethylaminopyridine dissolved in 10 ml of dichloromethane. The mixture was stirred for 5 hours at room temperature.

To the reaction solution was added a saturated aqueous solution of sodium bicarbonate, and the mixture was concentrated under reduced pressure. The residue obtained was dissolved in water-ethyl acetate, and the ethyl acetate layer was separated and concentrated under reduced pressure. The residue was adsorbed onto a silica gel column, whereupon 1.767 g of 1,3-diphenyl-2-propanol p-chlorobenzoate (75%) was isolated as an oily substance from the fraction eluted with ethyl acetate/n-hexane (15:1).

$^1$H—NMR (CDCl$_3$): δ 2.93 (d, 4H, J=6 Hz), 5.23~5.70 (m, 1H), 7.03~7.22 (m, 10H), 7.26 (d, 2H, J=8 Hz), 7.78 (d, 2H, J=8 Hz).

IR (neat): cm$^{-1}$ 3000, 1710, 1580, 1260, 1100, 1010, 750

150 mg of 1,3-diphenyl-2-propanol p-chlorobenzoate and 71 mg of carbazole were dissolved in 200 ml of a tetrahydrofuran-water mixture (20:1), and the solution was irradiated with a 100-W mercury lamp for 9 hours.

The reaction solution was concentrated under reduced pressure, and the residue was purified by preparative silica gel thin-layer chromatography (developer: ethyl acetate/n-hexane=1:20), whereupon 62 mg of the starting compound was recovered while 25 mg of 1,3-diphenylpropane (yield from the reacted starting compound 68%) was isolated.

EXAMPLE 4

The procedure of Example 3 was followed except that the carbazole was replaced by 71 mg of N-methylcarbazole, whereupon 57 mg of 1,3-diphenylpropane (yield 68%) was isolated.

EXAMPLE 5

150 mg of 1,3-diphenyl-2-propanol p-chlorobenzoate and 84 mg of 1,2,4,5-tetramethoxybenzene were dissolved in 200 ml of a tetrahydrofuran-water mixture (10:1), and the solution was irradiated with a 400-W mercury lamp for 10 hours.

Distillation of the solvent off from the reaction solution under reduced pressure was followed by purification of the residue by preparative thin-layer chromatography (developer: n-hexane/ethyl acetate=20:1) to produce 70 mg of 1,3-diphenylpropane (yield 83%).

EXAMPLE 6

Esterification was conducted with 0.61 ml of benzoyl chloride similarly as in Example 1 to obtain 1.248 g of 1,3-diphenyl-2-propanol benzoate (yield 75%) as an oily substance.

$^1$H—NMR (CDCl$_3$): δ 2.83 (d, 4H, J=6 Hz), 5.48 (t, 1H, J=6 Hz), 7.14 (s, 10H), 7.20~7.48 (m, 3H), 7.78~7.97 (m, 2H).

IR (neat): cm$^{-1}$ 1700, 1600, 1440, 1260, 1100, 1060, 700

150 mg of 1,3-diphenyl-2-propanol benzoate and 86 mg of N-methylcarbazole were dissolved in 200 ml of a tetrahydrofuran-water mixture (10:1), and the solution was irradiated with a 400-W mercury lamp for 9 hours.

The reaction solution was concentrated under reduced pressure, and the residue was purified by preparative silica gel thin-layer chromatography (developer: ethyl acetate/n-hexane=1:20), whereupon 50 mg of the starting compound was recovered while 73 mg of 1,3- diphenylpropane (yield from the reacted starting compound 82%) was isolated.

EXAMPLE 7

2.68 g of 3',5'-(1,1,3,3-tetraisopropyldisiloxy) adenosine was esterified similarly as in Example 1, purified by silica gel column chromatography (eluant: chloroform/methanol=20:1), and recrystallized to produce 2.577 g of 3',5'-(1,1,3,3-tetraisopropyldisiloxy)-2'-O-(m-trifluoromethylbenzoyl) adenosine (yield 70%) as a white crystal.

Melting point: 169° C.

Mass spectrum: 681 (M+) 638 (M+-43).

$^1$H—NMR (CDCl$_3$): δ 0.89 (s, 6H), 1.00~1.21 (m, 18H), 0.95~1.38 (m, 4H), 4.00~4.30 (m, 3H), 5.04~5.40 (m, 1H), 6.02 (d, 1H, J=6 Hz), 6.16 (s, 1H), 6.37~6.60 (m, 2H), 7.30~8.33 (m, 4H), 7.92 (s, 1H), 8.21 (s, 1H).

IR (in CHCl$_3$): cm$^{-1}$ 1730, 1630, 1340, 1240, 1220, 750.

100 mg of 3',5'-(1,1,3,3-tetraisopropyldisiloxy)-2'-O-(m-trifluoromethylbenzoyl)adenosine and 29 mg of 1,2,4,5-tetramethoxybenzene were dissolved in 200 ml of a tetrahydrofuran-water mixture (20:1), and the solution was irradiated with a 400-W mercury lamp for 4 hours.

To the reaction solution was added 100 ml of a saturated aqueous solution of sodium bicarbonate, and the mixture was concentrated under reduced pressure to approximately 100 ml. The solution thus concentrated was extracted with ethyl acetate, and the ethyl acetate layer was dried over magnesium sulfate. Subsequently, ethyl acetate was distilled off under reduced pressure, and the residue was purified by preparative thin-layer chromatography (developer: ethyl acetate/chloroform=2:1), whereupon 27 mg of the starting compound was recovered while 49 mg of 3',5'-(1,1,3,3-tetraisopropyldisiloxy)-2'-deoxyadenosine (yield from the reacted starting compound 93%) was isolated as an oily substance.

$^1$H—NMR (CDCl$_3$): δ 0.93~1.10 (m, 24H), 1.00~1.42 (m, 4H), 2.50~2.81 (m, 2H), 3.71~4.12 (m, 3H), 4.65~5.12 (m, 1H), 6.00~6.38 (m, 3), 7.97 (s, 1H), 8.23 (s, 1H).

IR (in CHCl$_3$): cm$^{-1}$ 1630, 1460, 1030, 880, 750.

High-resolution mass spectrum: Found: 493. 25342 Calcd. (C$_{22}$H$_{39}$N$_5$O$_4$Si$_2$) 493. 25402.

EXAMPLE 8

0.66 g of 2'-deoxyadenosine was esterified as in Example 1, purified by silica gel column chromatography (eluant: chloroform/methanol=20:1), and recrystallized to obtain 0.454 g of 3',5'-O-di(m-trifluoromethylbenzoyl)-2'-deoxyadenosine (yield 29%) as a white crystal.

Melting point: 160° C.

Mass spectrum: 595 (M+).

$^1$H—NMR (CDCl$_3$): δ 2.80~3.40 (m, 2H), 4.60~4.90 (m, 3H), 5.76~6.01 (m, 3H), 6.46 (t, 1H, J=6 Hz), 7.30~8.33 (m, 8H), 7.88 (s, 1H), 8.21(s, 1H).

130 mg of 3',5'-O-di(m-trifluoromethylbenzoyl)-2'-deoxyadenosine and 39.5 mg of N-methylcarbazole were dissolved in 50 ml of an isopropanol-water mixture (8:1), and the solution was irradiated with a 100-W high-pressure mercury lamp for 8 hours.

To the reaction solution was added 100 ml of a saturated aqueous solution of sodium bicarbonate, and the solvent was distilled off. The resultant solution was extracted with ethyl acetate, and the ethyl acetate layer was purified by preparative silica gel chromatography (developer: ethanol/chloroform=1:10), whereupon 78 mg of 2',3'-dideoxy-5'-(m-trifluoromethylbenzoyl)adenosine (yield 88%) was isolated in paste state.

High-resolution mass spectrum: Found: 407. 12116 Calcd. (C$_{18}$H$_{16}$N$_5$O$_3$F$_3$) 407. 12056.

$^1$H—NMR (CDCl$_3$): δ 2.20~2.80 (m, 4H), 4.39~4.70 (m, 3H), 6.23 (t, 1H, J=6 Hz), 6.25~6.50 (m, 2H), 7.29~8.23 (m, 4H), 7.93 (s, 1H), 8.20 (s, 1H).

IR (in CHCl$_3$): cm$^{-1}$ 1710, 1630, 1470, 1240, 1120, 750.

EXAMPLE 9

2.49 g of 2',5'-di-(t-butyldimethylsilyl)uridine was esterified as in Example 1 and purified by silica gel chromatography to produce 1.018 g of 2',5'-di-(t-butyldimethylsilyl)-3'-(m-trifluoromethylbenzoyl)uridine (yield 30%).

$^1$H—NMR (CDCl$_3$): δ 0.03 (s, 6H), 0.14 (s, 6H), 0.77 (s, 9H), 0.97 (s, 9H), 3.92~4.07 (m, 2H), 4.38~4.60 (m, 2H), 5.30~5.51 (m, 1H), 5.72 (d, 1H, J=8 Hz), 6.12 (d, 1H, J=5 Hz), 7.40~8.33 (m, 4H), 7.89 (d, 1H, J=8 Hz), 9.22 (b, s, 1H)

100 mg of 2',5'-di-(t-butyldimethylsilyl)-3'-(m-trifluoromethylbenzoyl)uridine and 30.7 mg of 1,2,4,5-tetramethoxybenzene were dissolved in 200 ml of a tetrahydrofuran-water mixture (20:1), and the solution was irradiated with a high-pressure mercury lamp for 4 hours in nitrogen atmosphere.

To the reaction solution was added 100 ml of a saturated aqueous solution of sodium bicarbonate, and the mixture was concentrated under reduced pressure to approximately 100 ml. The solution thus concentrated was extracted with ethyl acetate, and the extract was purified by silica gel column chromatography)(eluant: chloroform/methanol=20:1) to produce 53 mg of 2',5'-di-(t-butyldimethylsilyl)-3'-deoxyuridine (yield 75%).

$^1$H—NMR (CDCl$_3$): δ 9.44 (b, s, 1H), 8.18 (d, 1H, J5, 6=8.2 Hz), 5.72 (s, 1H), 5.63 (dd, 1H, J5, 6=8.2 Hz), 4.49 (dd, 1H), 4.35 (d, 1H, J4', 3'=3.8 Hz), 4.18 (dd, 1H, J5', 5'=11.9 Hz), 3.72 (dd, 1H, J5', 5'=11.9 Hz), 2.05 (ddd, 1H, J3', 3'=13.0 Hz), 1.71 (ddd, 1H, J3', 3'=13.0 Hz), 0.93, 0.90 (s, 18H), 0.17, 0.111, 0.106, 0.103 (3H, each)

EXAMPLE 10

2.52 g of 3',5'-(1,1,3,3-tetraisopropyldisiloxy)uridine was esterified as in Example 1 and purified by silica gel column chromatography (eluant: chloroform/methanol=20:1) to obtain 0.88 g of 3',5'-(1,1,3,3-tetraisopropyldisiloxy)-2'-(m-trifluoromethylbenzoyl) uridine (yield 25%).

$^1$H—NMR (CDCl$_3$): δ 0.83 (s, 6H), 1.02 (s, 6H), 1.10 (s, 12H), 0.80~1.20 (m, 4H), 4.00~4.26 (m, 3H), 4.38~4.65 (m, 1H), 5.59~5.70 (m, 1H), 5.71 (d, 1H, J=8 Hz), 5.96 (s, 1H), 7.20~7.83 (m, 2H, aromatic), 7.67 (d, 1H, J=8 Hz) 8.01~8.25 (m, 2H, aromatic), 9.90 (b, s, 1H)

100 mg of 3',5'-(1,1,3,3-tetraisopropyldisiloxy)-2'-(m-trifluoromethylbenzoyl)uridine and 29.6 mg of 1,2,4,5-tetramethoxybenzene were dissolved in 200 ml of a tetrahydrofuran-water mixture (20:1), and the solution was irradiated with a high-pressure mercury lamp for 6 hours.

The reaction solution was treated as in Example 9 to isolate 42.5 mg of 3',5'-(1,1,3,3-tetraisopropyldisiloxy)-2'-deoxyuridine (yield 60%).

$^1$H—NMR (CDCl$_3$): δ 7.72 (d, 1H, J5, 6=8 Hz), 6.04 (dd, 1H), 5.68 (d, 1H, J5, 6=8 Hz), 4.1 (m, 2H), 3.8 (m, 2H), 2.2~2.25 (m, 2H), 1.07, 0.99 (d, 32H)

Industrial Applicability

As has been set forth hereinbefore, the present invention provides for the first time a method for selective deoxygenation of the secondary and/or tertiary OH group(s) of the alcohol which can be suitably applied for industrial purposes and is therefore effective in converting a wide range of substances, such as natural substances, chemically synthesized substances and synthetic intermediates, having secondary and/or tertiary OH groups into more useful substances on an industrial scale by removing oxygen therefrom through the deoxygenation of the OH groups.

We claim:

1. A method for deoxygenation of an alcohol, wherein said alcohol has a secondary OH group, a tertiary OH group or both a secondary OH group and a tertiary OH group, by selectively deoxygenating said OH groups, which comprises subjecting the alcohol, whose OH groups to be deoxygenated have been esterified with substituted or unsubstituted benzoic acid, to a photocatalytic reaction in a hydrous or anhydrous hydrogen-donating solvent in the presence of an electron donor, said electron donor serving as a catalyst in the photocatalytic reaction which is not consumed during the reaction, or to an electrode reaction in the presence of an electrolyte for deoxygenation.

2. A method for deoxygenation of an alcohol as claimed in claim 1, wherein the deoxygenation is carried out by the photocatalytic reaction in the presence of an electron donor.

3. A method for deoxygenation of an alcohol as claimed in claim 2, wherein the electron donor is a compound having an oxidation-reduction potential not exceeding about 1.3 V.

4. A method for deoxygenation of an alcohol as claimed in claim 3, wherein the electron donor is selected from the group consisting of aromatic hydrocarbons, aromatic heterocyclic compounds, olefinic compounds, amines, phenols, aminophenols, carboxylic acids, and azo compounds, all having an oxidation-reduction potential not exceeding about 1.3 V.

5. A method for deoxygenation of an alcohol as claimed in claim 1, wherein the substituent of the substituted benzoic acid is an electron withdrawing substituent situated at the meta- or para-position of the benzoyl group of the benzoic acid.

6. A method for deoxygenation of an alcohol as claimed in claim 5, wherein the substituent is selected from the group consisting of halogenoalkyl, halogen, alkyl- or arylsulfonyl, and acyl.

7. A method for deoxygenation of an alcohol as claimed in claim 1, wherein the hydrogen-donating solvent is selected from the group consisting of ether solvents and alkanol solvents.

8. The method according to claim 1, wherein the electron donor is a compound having the property of re-accepting an electron from radical species generated by the photocatalytic reaction.

9. The method according to claim 1, wherein the electron donor is a compound that can be recovered for reuse after completion of the reaction.

* * * * *